United States Patent
Ogura et al.

(10) Patent No.: US 6,521,224 B1
(45) Date of Patent: Feb. 18, 2003

(54) METHOD FOR CONTROLLING INJURIOUS INSECT

(75) Inventors: Koichi Ogura, Saitama (JP); Kinya Ogawa, Kanagawa (JP); Takehiko Fukumoto, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 1563 days.

(21) Appl. No.: 08/665,046

(22) Filed: Jun. 7, 1996

Related U.S. Application Data

(63) Continuation of application No. 08/480,023, filed on Jun. 7, 1995, now abandoned, which is a continuation of application No. 08/393,238, filed on Feb. 23, 1995, now abandoned, which is a continuation of application No. 08/080,404, filed on Jun. 21, 1993, now abandoned.

(30) Foreign Application Priority Data

Jul. 3, 1992 (JP) ............................................. 4-176747

(51) Int. Cl.⁷ ........................ A01N 25/18; A01N 25/00; A01N 25/34
(52) U.S. Cl. ........................ 424/84; 424/405; 424/409; 424/411; 424/412; 424/417
(58) Field of Search ........................ 424/84, 405, 408, 424/409, 411, 414, 417, 412

(56) References Cited

U.S. PATENT DOCUMENTS

| | | | | |
|---|---|---|---|---|
| 4,600,146 A | * | 7/1986 | Ohno | 239/6 |
| 4,639,393 A | * | 1/1987 | Von Kohorn et al. | 43/111 |
| 4,879,837 A | * | 11/1989 | Capizzi et al. | 43/124 |
| 5,236,715 A | * | 8/1993 | McDonough et al. | 424/484 |

FOREIGN PATENT DOCUMENTS

JP 59190902 * 10/1984

OTHER PUBLICATIONS

Pesticide & Toxic Chemical News, vol. 19(11), Jan. 16, 1991, "Exemptions From Tolerance Requirements Granted During 1990."*
Qureshi et al. "Control of Pink Bollworm . . . " Pak. J. Sci. Ind. Res., vol. 31(10), pp. 711–713 (1988); abstracted din Biological Abstracts 87(6):57716 (1989).*
CABA Abstract 84:36633 (1983).*
Biological Abstracts 66: 26515 (1978).*
Qureshi et al., "Control of Pink Bollworm, *Pectinophora gossypiella* (Saunders) By Mating Disurption Technique," Pakistan J. Sci. Ind. Res., vol. 31 (10), 1988, pp. 711–713.*

* cited by examiner

*Primary Examiner*—John Pak
(74) *Attorney, Agent, or Firm*—Reed Smith LLP

(57) ABSTRACT

A method for controlling an injurious insect is herein disclosed, which comprises disturbing the copulative communication of an injurious insect to prevent proliferation of the insect by distributing a source of the sex pheromone thereof over a field to be controlled to make the sex pheromone release from the source distributed in the field, wherein a source of the sex pheromone having a high effective component-release rate per unit time is distributed over the central region of the field at a low density while a source of the sex pheromone having a low effective component-release rate per unit time is distributed over the peripheral region of the field at a high density. A sex pheromone-release agent having an effective component-release rate ranging from 0.01 to 2 g/day may be distributed over the central region of the field at a density ranging from 1 to 50 locations/ha, while a sex pheromone-release rope having an effective component-release rate ranging from 5 to 250 mg/m/day may be substantially uniformly stretched around the peripheral region of the field at a density ranging from 10 to 150 m/ha.

2 Claims, No Drawings

METHOD FOR CONTROLLING INJURIOUS INSECT

This is a continuation of application Ser. No. 08/480,023 filed Jun. 7, 1995 now abandoned, which, in turn, is a continuation of aplication Ser. No. 08/393,238 filed Feb. 23, 1995, now abandoned, which, in turn, is a continuation of application Ser. No. 08/080,404 filed Jun. 21, 1993 now abandoned.

BACKGROUND OF THE INVENTION

The present invention relates to an injurious insect-control method for controlling the proliferation of the injurious insect by disturbing the communication of the injurious insect for copulation through release of the sex pheromone of the insect from a source thereof distributed over a field.

The copulation of an injurious insect can be disturbed by releasing, in a large amount, the sex pheromone of the insect which is emitted by the female insect for making the male insect realize the location of the former. Such an injurious insect-control method has recently become of major interest since it allows the reduction of the amount of an agricultural chemical used in a field for controlling an injurious insect and has been considered to be a promising method.

Conventionally, there has seldom been investigated any method for effectively controlling an injurious insect by rationally distributing a sex pheromone-release agent throughout a very wide field. It is not easy to distribute, for instance, an agent for releasing the sex pheromone of a specific injurious insect over a field. In addition, the labor and time required for the distribution thereof in a field increase in proportion to the area of the field which requires the control of the injurious insect.

There have been developed so-called spray type sex pheromone-release agents which are subjected to the aerial application for the purpose of saving the labor required for the distribution of the agents over fields. However, this aerial distribution of the spray type sex pheromone-releasing agent does not ensure a sufficient injurious insect-control effect. The effects of the spray type sex pheromones are greatly influenced by various external factors such as meteorological conditions. For this reason, it is very difficult to appropriately select the time for distributing the sex pheromone-releasing agent and any desired effect thereof would not be anticipated when missing the chance for its application. There has been known an agent having a long effective period. In this case, however, the agent suffers from a variety of problems. For instance, the amount of the agent released per unit time period lacks in uniformity.

SUMMARY OF THE INVENTION

The object of the present invention is to eliminate the foregoing drawbacks associated with the conventional methods and more specifically to provide a method for rationally controlling injurious insects which permits the reduction of the labor and time required for the distribution of the sources of sex pheromones of these injurious insects over fields to be controlled and which permits effective control of the injurious insects.

The method for controlling an injurious insect according to the present invention comprises disturbing the copulative communication of the insect to prevent proliferation of the insect by distributing a source of the sex pheromone thereof over a field to thus make the sex pheromone release from the source distributed in the field, wherein a source of the sex pheromone having a high effective component-release rate per unit time is distributed over the central region of the field at a low density while a source of the sex pheromone having a low effective component-release rate per unit time is distributed over the peripheral region of the field at a high density.

In a preferred embodiment according to the present invention, a sex pheromone-release agent having an effective component-release rate ranging from 0.01; to 2 g/day may be distributed over the central region of a field at a density ranging from 1 to 50 locations/ha, while a sex pheromone-release rope having an effective component-release rate ranging from 5 to 250 mg/m/day may be stretched around the peripheral region of the field at a density ranging from 10 to 150 m/ha.

DETAILED EXPLANATION OF THE INVENTION

The injurious insect-control method according to the present invention comprises the step of distributing the sources of the sex pheromone of an injurious insect over a field. The kinds of effective components of the sex pheromone-release agents to be distributed in a field are appropriately selected depending on the kinds of injurious insects to be controlled. Examples of injurious insects which can be controlled according to the method of the present invention are those belonging to the order of lepidopteron such as *Spodoptera litura Fabricius*, Egyptian cotton leafworm, pink bollworm, and *Heliothis assulta* GUENEE.

The amount (per unit area of a field) of a sex pheromone to be released from a source thereof distributed over a field is, in principle, selected depending on the area of the field, conditions of field products and vermination-conditions of individual injurious insects to be controlled. More specifically, a sex pheromone-release agent having an effective component-release rate ranging from 0.01 to 2 g/day is distributed in the central region of a field to be controlled at a density ranging from 1 to 50 locations/ha. On the other hand, a sex pheromone-release agent having an effective component-release rate ranging from 0.001 to 0.05 g/day is uniformly distributed around the peripheral region of the field at a density ranging from 500 to 2000 locations/ha. In other words, a sex pheromone-release agent having a high release rate per unit time is distributed over the central region of a field to be controlled at a low density, while a sex pheromone-release agent having a low effective component-release rate (per unit time) is distributed over the peripheral region of the field at a high density.

The distribution of the sex pheromone-release agent around the periphery of the field may be performed by stretching a rope in which the sex pheromone-release agent is enclosed. The effective component-release rate of the rope enclosing the sex pheromone-release agent preferably ranges from 5 to 250 mg/m/day. Such a sex pheromone-release rope is stretched around the periphery of a field at a density ranging from 10 to 150 m/ha.

The present invention will hereinafter be described in more detail with reference to the following working Examples, but the present invention is by no means limited to these specific Examples.

EXAMPLE 1

On May, a sex pheromone-release agent for controlling pink bollworm (effective component-release rate: 140 mg/day) was distributed over the central region of a cotton field having a whole area of 900 ha at a density of 10 locations/ha, while a sex pheromone-release rope in which the sex pheromone had been enclosed (sex pheromone-release rate: 50 mg/m/day) and which had a length of 12000 m was stretched around the periphery of the cotton field. After 3 months, the number of larvae per 100 cotton seeds was determined. The results thus obtained are listed in the following Table 1.

Comparative Example 1

A sex pheromone-release agent for controlling pink bollworm (effective component-release rate: 140 mg/day) was distributed over the central region of a cotton field under the same conditions used in Example 1 and at the same time identical to that at which the sex pheromone-release agent was distributed in Example 1. The agent was distributed at a density of 10 locations/ha. Neither sex pheromone-release agent nor sex pheromone-release rope was distributed over or stretched around the peripheral region of the cotton field. The number of larvae per 100 cotton seeds was determined in the same manner used in Example 1. The results thus obtained are listed in Table 1.

Comparative Example 2

A sex pheromone-release agent for controlling pink bollworm (available from SHIN-ETSU. CHEMICAL CO., LTD. under the trade name of PB-ROPE; effective component-release rate: 1 mg/day) was distributed over a cotton field and at the same time identical to those used in Example 1. The agent was uniformly distributed at a density of 1000 locations/ha throughout the whole area of the cotton field. Thereafter, the number of larvae per 100 cotton seeds was determined in the same manner used in Example 1. The results thus obtained are listed in Table 1.

TABLE 1

| Ex. No. | Distribution Density (location/ha) | Number of Larvae (Number per 100 cotton seeds) |
| --- | --- | --- |
| 1 | 10 | 12 |
| 1* | 10 | 25 |
| 2* | 1000 | 10 |

*Comparative Example

EXAMPLE 2

The same procedures used in Example 1 were repeated. More specifically, a sex pheromone-release agent having an effective component-release rate of 260 mg/day was distributed over the central region of the cotton field and the sex pheromone-release agent used in Comparative Example 2 was distributed at the periphery of the cotton field. These agents were distributed at densities of 5 locations/ha and 1000 locations/ha respectively. Thereafter, the number of larvae per 100 cotton seeds was determined for the central region and the peripheral region. The results thus obtained are listed in Table 2.

EXAMPLE 3

The same procedures used in Example 1 were repeated. More specifically, the sex pheromone-release rope used in Example 1 was stretched around the periphery of the cotton field, while the central region of the field was treated in the same manner used in Example 2. The number of larvae per 100 cotton seeds was determined. The results thus obtained are listed in Table 2.

EXAMPLES 4 AND 5

The same procedures used in Example 1 were repeated. More specifically, a sex pheromone-release agent having an effective component-release rate of 1600 mg/day was distributed over the central regions of the cotton fields. The agent was distributed at a density of 1 location/ha. On the other hand, the peripheral regions of the cotton fields were treated in the same manner used in Examples 2 and 3. The number of larvae per 100 cotton seeds was determined. The results thus obtained are listed in Table 2.

Comparative Example 3

The same procedures used in Example 1 were repeated. More specifically, neither sex pheromone-release agent nor sex pheromone-release rope was distributed over or stretched around the peripheral region of a cotton field, while the central region of the field was treated in the same manner used in Example 5. The number of larvae per 100 cotton seeds was determined. The results thus obtained are listed in Table 2.

Comparative Example 4

Cotton seeds were harvested from a cotton field under the same conditions as those for the field used in Example 1, provided that any sex pheromone-release agent was not distributed over the field. The number of larvae was evaluated at the same time identical to that at which the sex pheromone-release agent was distributed in Example 1. The results are listed in Table 2.

TABLE 2

| Ex. No. | 2 | 3 | 4 | 5 | 3* | 4* |
| --- | --- | --- | --- | --- | --- | --- |
| Central Region | | | | | | |
| Density (location/ha) | 5 | 5 | 1 | 1 | 1 | 0 |
| Release Rate (mg/unit dose/day) | 260 | 260 | 1600 | 1600 | 1600 | — |
| Peripheral Region | | | | | | |
| Density (location/ha) | 1000 | (rope) | 1000 | (rope) | 0 | 0 |
| Release Rate (mg/unit dose/day) | 1 | (5) | 1 | (5) | — | — |
| Number of Larvae per 100 cotton seeds | 18 | 14 | 24 | 16 | 39 | 88 |

*Comparative Example
Note: In Table 2, the release rate of the rope is expressed in terms of mg/m/day.

The foregoing results clearly indicate that the distribution of sex pheromone-release agent, having a high effective component-release rate, over the central region of a field to be controlled ensures an injurious insect-control effect almost comparable to that observed in Comparative Example 2 in which a sex pheromone-release agent having a low effective component-release rate was uniformly distributed throughout a field to be controlled at a high density.

What is claimed is:

1. A method for controlling injurious insects in a field by disturbing the copulative communication of the insects to prevent proliferation of the insects by releasing a sex pheromone of the insect comprising substantially uniformly distributing sources of the sex pheromone having an effective component-release rate of 0.01 to 2 g/day over the central region of the field at 1 to 50 locations/ha, and substantially uniformly distributing sources of the sex pheromone having an effective component-release rate of 0.01 to 0.05 g/day over the peripheral region of the field at 500 to 2000 locations/ha.

2. The method of claim 1 wherein the sources used for the peripheral region are a pheromone-release rope having an effective component-release rate of 5 to 250 mg/m/day, said rope being substantially uniformly stretched over the peripheral region at a density of 10 to 150 m/ha.

* * * * *